US00PP34120P2

(12) United States Plant Patent
Yakligian

(10) Patent No.: US PP34,120 P2
(45) Date of Patent: Apr. 12, 2022

(54) '1898 AZ'

(50) Latin Name: *Prunus persica*
Varietal Denomination: 1898 AZ

(71) Applicant: James Yakligian, Sanger, CA (US)

(72) Inventor: James Yakligian, Sanger, CA (US)

( * ) Notice: Subject to any disclaimer, the term of this patent is extended or adjusted under 35 U.S.C. 154(b) by 0 days.

(21) Appl. No.: 17/524,702

(22) Filed: Nov. 11, 2021

(51) Int. Cl.
*A01H 6/74* (2018.01)
*A01H 5/08* (2018.01)

(52) U.S. Cl.
USPC ..... Plt./197

(58) Field of Classification Search
USPC ..... Plt./197
See application file for complete search history.

(56) References Cited

U.S. PATENT DOCUMENTS

| | | | |
|---|---|---|---|
| PP9,438 | P | 1/1996 | Doyle |
| PP15,496 | P2 | 6/2005 | Slaughter et al. |
| PP26,901 | P2 | 7/2016 | Yakligian |
| PP28,340 | P2 | 8/2017 | Caprelian |

*Primary Examiner* — Annette H Para
(74) *Attorney, Agent, or Firm* — Sierra IP Law, PC; Mark D. Miller

(57) ABSTRACT

A new and distinct variety of peach tree which is somewhat similar to the 'Calara' peach tree (U.S. Plant Pat. No. 15,496) from which it is distinguished by producing fruit hat ripens a month after the harvesting period of 'Calara' in a normal year.

7 Drawing Sheets

BACKGROUND OF THE NEW VARIETY

The present invention refers to a new variety of peach tree which will hereinafter be denominated as the '1898 Peach' which produces clingstone fruit which are mature for commercial harvesting and shipment in late October in a normal growing year in the San Joaquin Valley of Central California as a very firm, very late, fresh market peach with a good red blush coloration.

In the development of new commercial varieties of fruit specific characteristics places a premium on those varieties, which are early or late maturing, in the growing season. However, many such varieties have small size, lack of flavor, or coloration. In some instances there are other undesirable characteristics that decrease the commercial success. In order for a fruit to be a commercial success it must possess those characteristics of good size, good color, and good flavor. At the same time the date of maturity must be separate or different than other similar fruit. The fruit of the present variety also tends to retain its firmness longer than other peaches. This new variety meets all of the aforementioned criteria and therefore is of commercial appeal to the consumer.

ORIGIN AND ASEXUAL REPRODUCTION OF THE NEW VARIETY

The present variety of peach tree was discovered by the inventor in a grove of 'Calara' peach trees (U.S. Plant Pat. No. 15,496) located near Parlier, Calif. The inventor discovered the new variety as a branch/sport on a 'Calara' tree in the year 2020 and observed it for one year. The new variety was asexually reproduced in 2021 by bud grafting approximately 80 trees onto 'Nemaguard' (unpatented) rootstock in a nearby orchard. These trees have not yet produced fruit. However, fruit was obtained from the parent (sport).

The inventor has carefully examined the asexually reproduced trees which appear to be identical to the parent.

SUMMARY OF THE NEW VARIETY

The subject '1898 Peach' variety is characterized by producing a large, firm clingstone fruit which has good red blush coloration and is ripe for commercial harvesting and shipment approximately the third and fourth week of October in the San Joaquin Valley of Central California. The new variety is similar to 'Calara' (U.S. Plant Pat. No. 15,496), but from which is distinguishable in that the fruit ripens a month later than 'Calara', between October 15 and November 1 in a normal year. The fruit of this new variety is very firm, and possesses a very good flavor as well as an aroma that is greatly acceptable for a late ripening variety.

BRIEF DESCRIPTION OF THE DRAWINGS

The accompanying drawings are color photographs showing fruit and foliage of the new variety.

DETAILED DESCRIPTION

Figure 1:
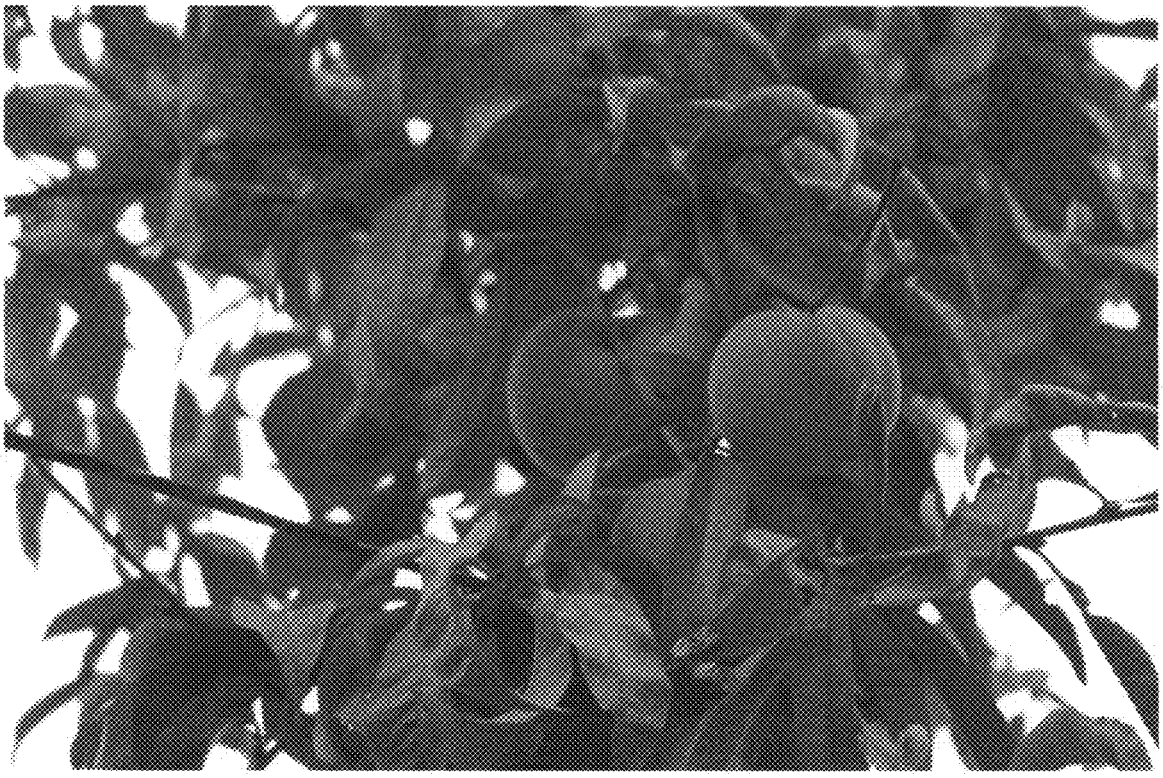
FIG. 1 shows branches, leaves and fruit of the new variety in situ.
Figure 2:
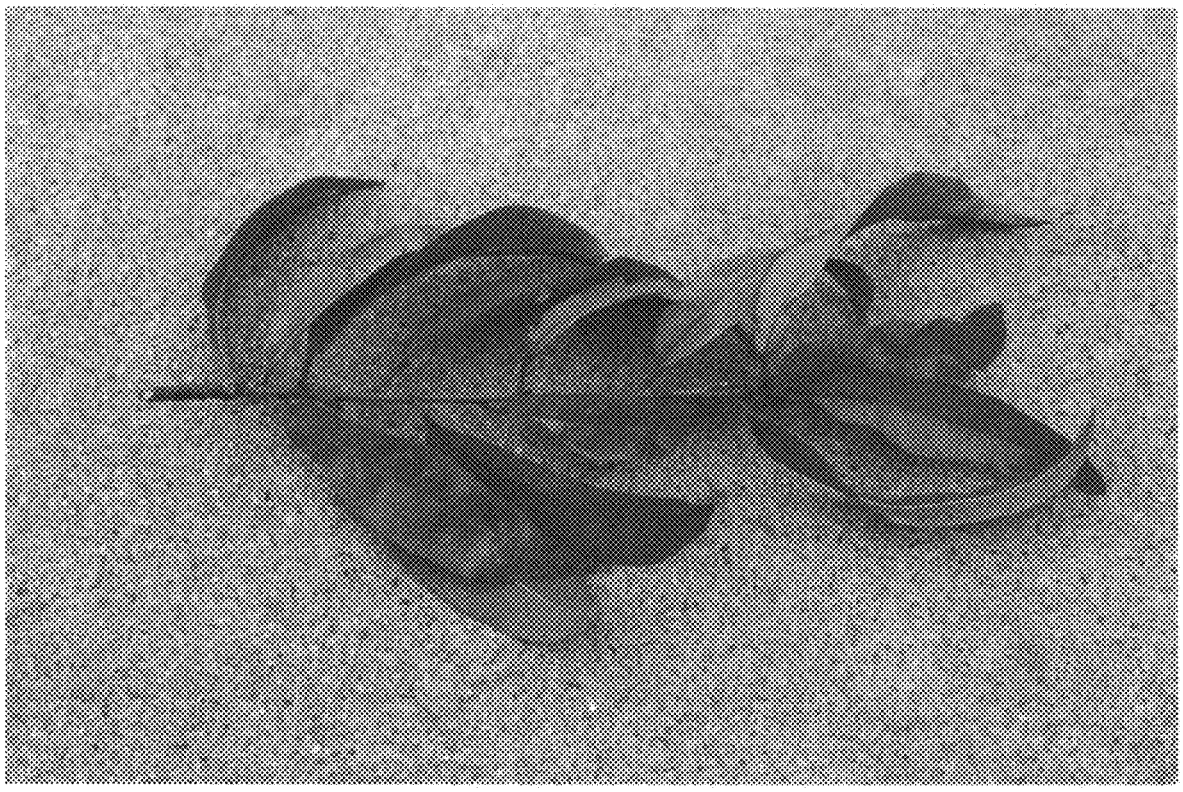
FIG. 2 shows a close up of the tops of leaves and branches of the new variety.
Figure 3:
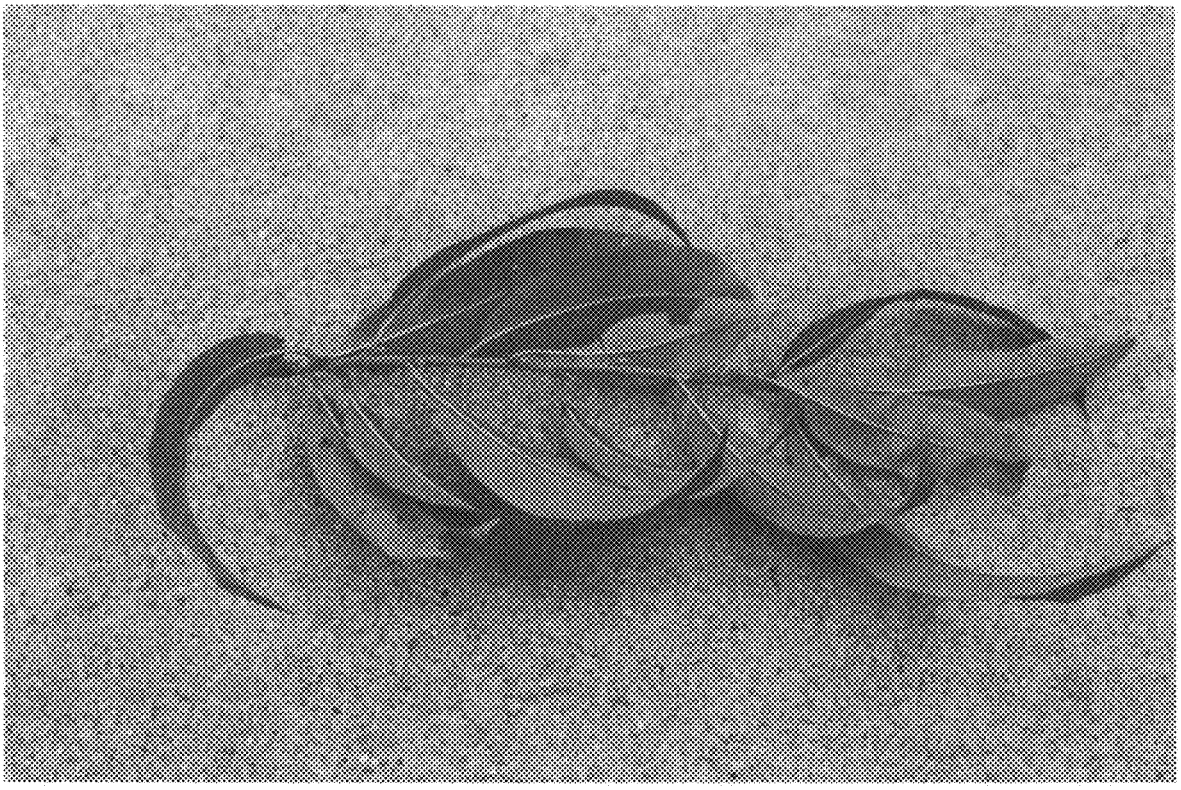
FIG. 3 shows a close up of the undersides of leaves and branches of the new variety.
Figure 4:
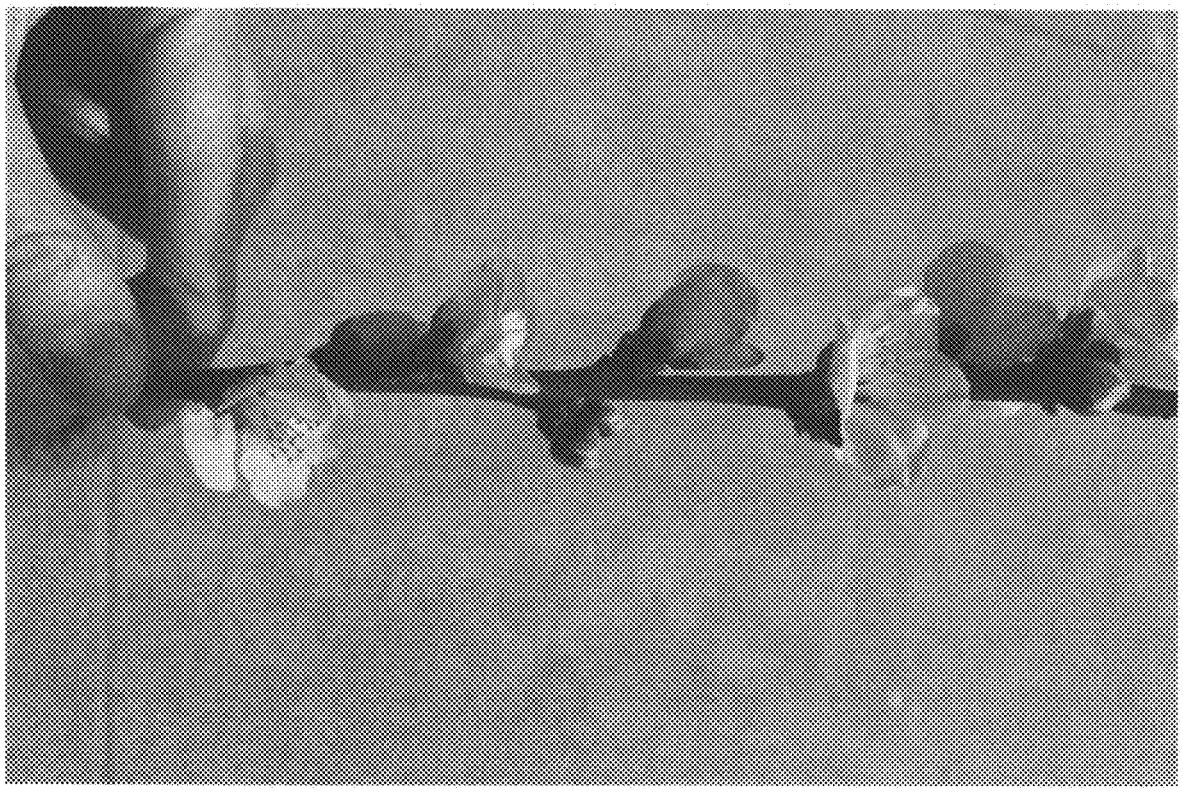
FIG. 4 shows a branch of the new variety with flowers and buds.
Figure 5:
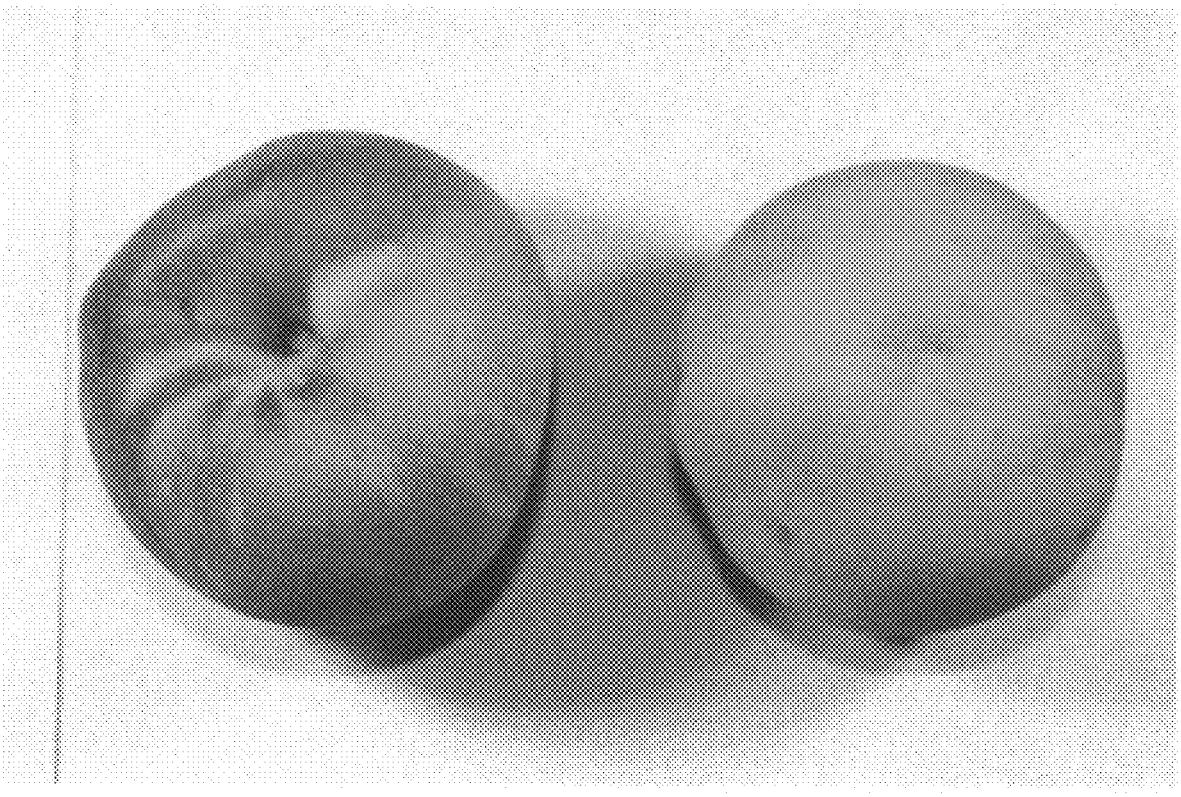
FIG. 5 shows whole uncut fruit of the new variety.
Figure 6:
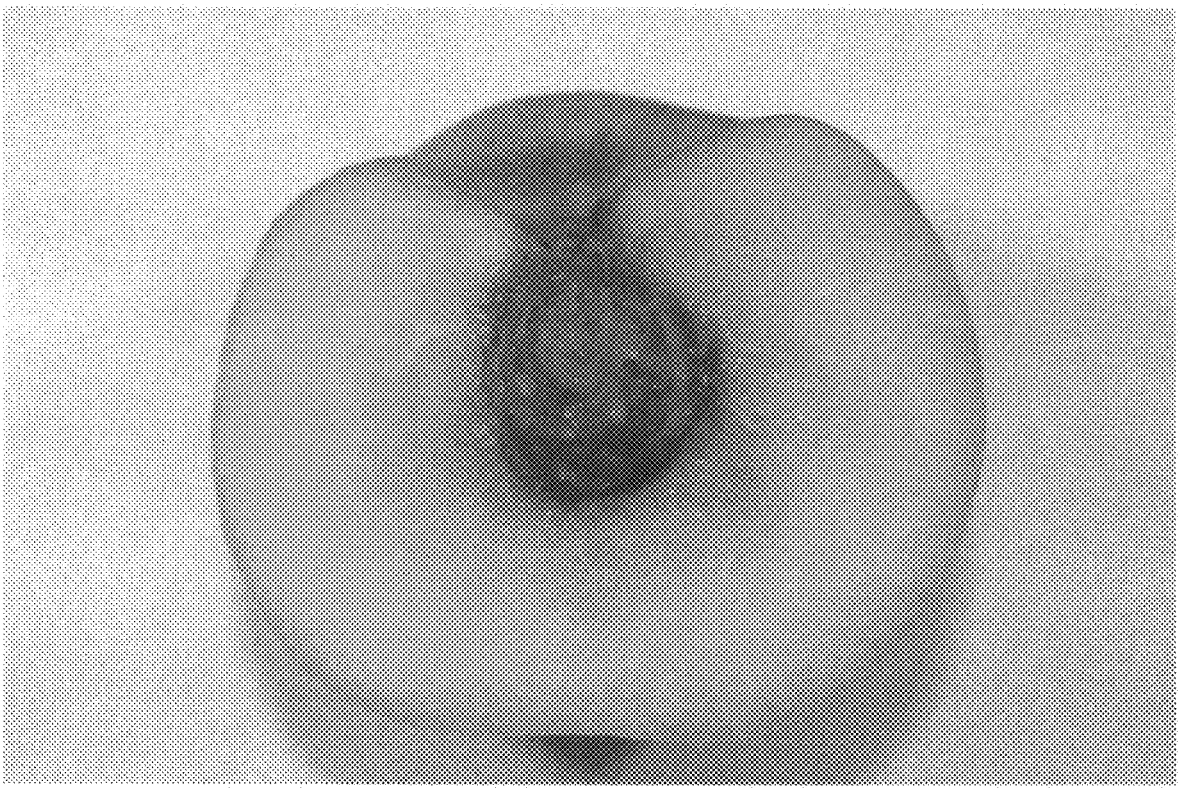
FIG. 6 shows a piece of fruit cut in half showing the pit and the flesh.
Figure 7:
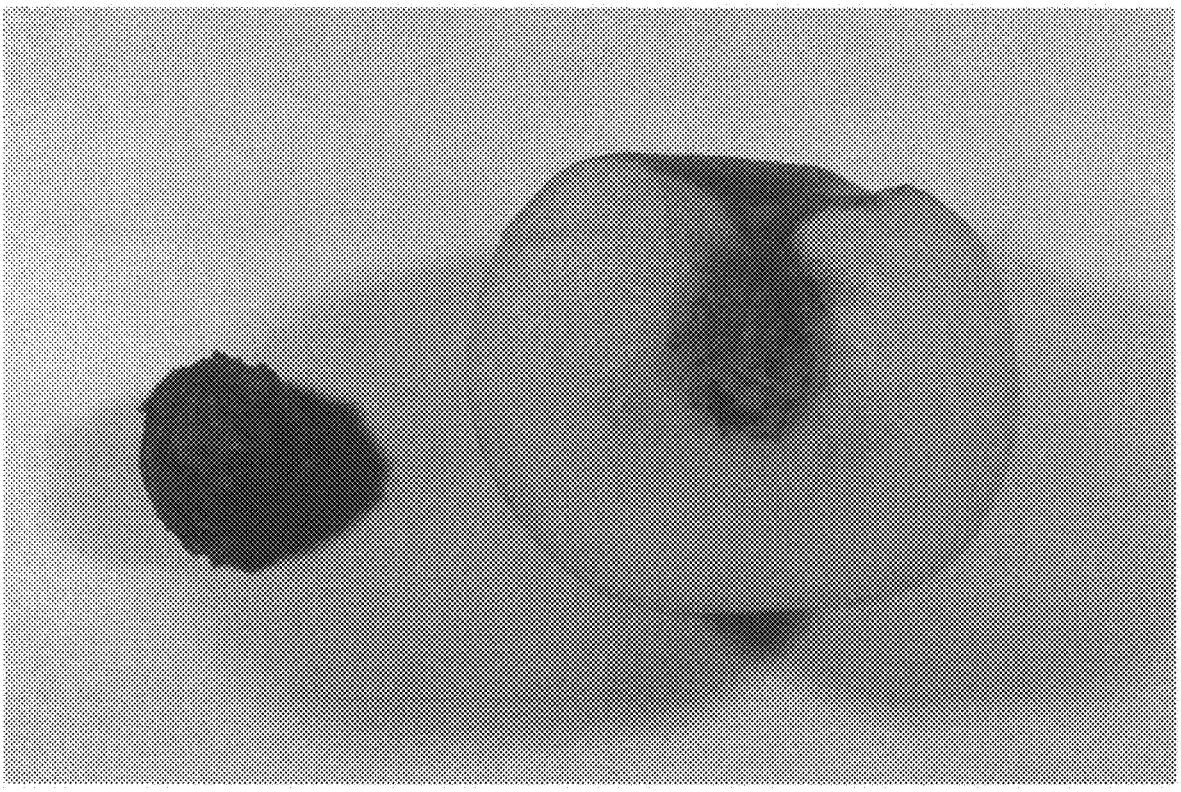
FIG. 7 shows a piece of fruit cut in half showing the pit removed from the flesh.

Referring more specifically to the pomological description of this new and distinct variety of peach tree, the following has been observed under the ecological conditions prevailing in the location of origin which is near Sanger, Calif. in the San Joaquin Valley of Central California. All major color code designations are by reference to the Dictionary of Color by Maerz & Paul, First Edition 1930. Common color names are also occasionally employed.

TREE

Size: Tree is similar in size and growth habit to 'Calara'. Considered medium-large for peaches.
Vigor: Moderate.
Form: Upright.
Regularity of bearing appears to be regular (i.e., every year, not in alternate years).
Trunk size: Medium.
Branches:
*Size*.—Medium.
*Surface texture*.—Slightly rough. a. Mature — Slightly Rough. b. Immature — Smooth.
*Color code* (*one year or older*).—Bronze-umber, 15-J-11.
*Color code* (*immature*).—Biscay green, 21-K-5.

LEAVES

Size: Medium to large.
Length: 95-113 mm.
Width: 21-32 mm.
Shape: Lanceolate to nearly linear, leaf tip acuminate.
Texture: Smooth.
Color code:
*Upwardly disposed surface* (*upper side*).—Hellebore green, 23-L-3.
*Downwardly disposed surface* (*underside*).—Close to "palm", 22-K-2.
Marginal form: Crenate to serrate, slightly undulate in larger leaves.
Leaf base: Acute.
Leaf vein:
*Color code*.—Linden green, 19-J-1.
*Thickness*.—0.5-1.0 mm.
Glandular characteristics:
*Reniform*.—Alternate.
*Color*.—Cocoa turtle apache+, sahara−, 7-E-12.
*Size*.—0.5-1 mm.
*Number*.—2-4.
Petiole:
*Size*.—Medium.
*Length*.—From 5 -9 mm.
*Diameter*.—From 1 -2 mm.
*Color code*.—Citron green, 19-K-2.
Stipules: Deciduous, only present in young leaves, in pairs at petiole base.
*Length*.—From 8-10 mm.
*Width*.—From 0.5-1 mm.
*Shape*.—Linear.
*Color code*.—Bright green, 21-L-7.

FLOWERS

Flower buds: Hardy under typical central San Joaquin Valley climate condition.
*Size*.—Dormant buds of average size.
*Length*.—From 10-14 mm.
*Form*.—Ellipsoidal.
Bud scales:
*Color*.—Bonito Fuscous+(7-C-7) and pubescent on outer surface, Briarwood+(8-J-6) on inner surface.
Generally: Showy type.
Date of bloom: 100% bloom as of approximately March 12.
Size: Generally medium to large.
Diameter: When fully expanded: 36-43 mm.
Bloom quantity: Abundant.
Fragrance, slight: Typical peach.
Petals:
*Size*.—Medium to large. Length — 16 mm to 18 mm. Width — 15 mm to 17 mm.
*Form*.—Broadly ovate to almost round.
*Number*.—Five.
*Color*.—Pink (41-K-1) near claw to very very light pink (41-B-1) at apex margins.
*Petal claws*.—Broadly truncate. Width — 1 mm-1.5 mm. Length — 1 mm-1.5 mm.
*Petal margins*.—Moderately undulated with somewhat rounded margins.
*Flower pedicel*.—Very short 3-4 mm. Color — Courge green (21-L-3). Surface — glabrous. Diameter — 2-3 mm.
Sepals:
*Surface*.—Pubescent.
*Size*.—Medium to large.
*Form*.—Ovate.
*Color*.—Maroon (55-L-5) at base, to gray-green (21-E-2) along sepal lobe edges, with green color (21-K-7) inside of sepals.
*Number*.—Five.
Hypanthium:
*Outside color*.—Courge green (21-L-3) at base grading into maroon (55-L-5) near base of sepals.
*Inside of hypanthium, color*.—Navaho (10-D-12).
Anthers:
*Size*.—Average.
*Color*.—Gold tinged with pink (3-A-11).
Pollen: Present, yellow ochre (11-L-7).
Stamen: 8-13 mm.
*Number*.—35-45.
Filament:
*Color*.—White (49-A-1) to Persian Lilac (51-H-1).
Position of stamens relative to petals: Same level.
Pistil:
*Length*.—Average 16 mm.
*Number*.—One.
*Color*.—Light green (17-I-2) at the base, grapefruit (19-L-1) at the top.
*Surface*.—Pubescent.
Stigma:
*Color*.—Yellow-green (20-L-1).
Ovary: Pubescent, ovary densely covered with unbranched, multicellular trichomes.
Position of stigma relative to anthers: Same level.

FRUIT

Date of maturity: October 15$^{th}$ to November 1$^{st}$ in a normal year.
Size:
*Diameter axial plane*.—From 67-70 mm.
*Transverse in suture plane*.—From 67-70 mm.
*Transverse at rt. angle to suture plane*.—From 69-71 mm.

Form:
*Uniform.*—
*Symmetrical or asymmetrical.*—Shape of fruit is slightly asymmetrical.
Suture: Shallow.
Ventral surface: Uneven.
Stem cavity:
*Width.*—From 4-7 mm.
*Depth.*—From 13-17 mm.
*Length.*—From 5-7 mm.
*Shape.*—Oval.
Stem: Short.
*Diameter.*—From 2-4 mm.
Apex: Rounded to slight depressed.
Pistil point: Slightly raised above surface, with a depression on either side in the suture axis.
Skin: Thickness normal for peach, medium pubescence.
Texture: Firm.
Color code:
*Blush color.*—Deep pinkish orange, 4-K-11 to 4-I-11.
*Ground color.*—Varies over 50% at axis, from yellow to orange, 9-L-5 to 9-L-8.
*Flesh color.*—Spanish yellow-golden yellow, 10-L-7.
*Color at surface of pit cavity.*—Flirt-India red to Arabian red+/red robin−, 2-K-9 to 7-L-6.
*Color of pit well.*—Brigand, 2-J-11.
Juice production: Moderate.
Flavor: Good.
Aroma: Good.
Fruit sweetness: Medium.
Fibers:
*Number.*—Few.
*Texture.*—Firm.
Ripening: Even.
Eating quality: Good.

Stone:
*Attachment.*—Clingstone.
*Fibers.*—Numerous, Short, slightly thick.
*Size.*—Medium. Length — from 27-28 mm. Width — from 22-25 mm. Diameter — from 18-19 mm.
Form:
*Ovate.*—Round.
Apex: Sharply acute.
Color code, when dry: Cordova-Castellon+(light brown), 7-J-11.
Base: Truncate.
Sides: Unequal.
Texture: Pitted.
Ridges: On both sides of stone and narrowing towards apex; ridge on one side of the stone is much stronger (i.e., multiple ridges present on that side).
Tendency to split: None evident externally, although there is always a deeper suture in the flesh on one side of the stem cavity.
Use: Fresh Market.
Shipping and quality: Very Good.

The above description of this new variety of peach tree is based on the growing conditions prevailing near Parlier, Calif. in the Central San Joaquin Valley of California, variations of the usual magnitude and characteristics may occur due to change in cultural factors, including irrigation, fertilization, primary climatic changes, et al.

What is claimed is:

1. A new and distinct variety of peach tree as described and illustrated which is somewhat similar to 'Calara' (U.S. Plant Pat. No. 15,496), from which it is distinguished by producing fruit that ripens a month after the harvesting period of 'Calara', with good exterior coloration and very good eating quality which are mature for commercial harvesting and shipment approximately October 15-November 1 in a normal year.

* * * * *